United States Patent [19]

Bahrmann et al.

[11] 4,289,913
[45] Sep. 15, 1981

[54] PROCESS FOR PREPARING 3-(4)-FORMYLTRICYCLO-[5,2,1,0$^{2,6}$]-DECENE-8

[75] Inventors: Helmut Bahrmann, Hünxe; Jürgen Weber, Oberhausen; Boy Cornils, Dinslaken, all of Fed. Rep. of Germany

[73] Assignee: Bayer Aktiengesellschaft, Leverkusen, Fed. Rep. of Germany

[21] Appl. No.: 99,121

[22] Filed: Nov. 30, 1979

[30] Foreign Application Priority Data

Jul. 13, 1979 [DE] Fed. Rep. of Germany ....... 2928313

[51] Int. Cl.$^3$ ............................................... C07C 45/50
[52] U.S. Cl. .................................................. 568/444
[58] Field of Search ........................ 260/598; 568/444

[56] References Cited

U.S. PATENT DOCUMENTS 3,956,177 11/1976 Zuech ................................ 568/444
4,052,461 10/1977 Tinker et al. ..................... 260/598
4,146,505 3/1979 Weber et al. ..................... 260/598

FOREIGN PATENT DOCUMENTS 928645 7/1949 Fed. Rep. of Germany ...... 260/598
1576057 7/1969 France .............................. 260/598
801734 9/1958 United Kingdom ............... 260/598

Primary Examiner—Natalie Trousof
Assistant Examiner—James H. Reamer
Attorney, Agent, or Firm—Sprung, Felfe, Horn, Lynch & Kramer

[57] ABSTRACT

A process for preparing 3- or 4-formyltricyclo-[5,2,1,0$^{2,6}$]-decene-8 which comprises contacting dicyclopentadiene with carbon monoxide and hydrogen in the presence of a rhodium catalyst at 110° to 150° C. and 50 to 400 atmospheres, said catalyst being present in an amount of 1 to 30 ppm of rhodium, based upon the amount of dicyclopentadiene employed, said rhodium being present in the form of an organic phosphine-carbon monoxide containing complex.

14 Claims, No Drawings

PROCESS FOR PREPARING 3-(4)-FORMYLTRICYCLO-[5,2,1,0$^{2,6}$]-DECENE-8

BACKGROUND OF THE INVENTION

1. Field of the Invention

The present invention relates to a process for preparing 3- and 4-formyltricyclo-[5,2,1,0$^{2,6}$]-decene-8 by hydroformylating dicyclopentadiene. By virtue of the presence of two double bonds, dicyclopentadiene can form both monoaldehydes and dialdehydes when reacted with carbon monoxide and hydrogen in the presence of carbonyl-forming metals of Group VIII of the Periodic System.

2. Discussion of the Prior Art

The preparation of the dialdehyde, namely, the chemical compound tricyclodecane-dialdehyde from dicyclopentadiene, is described in German Pat. No. 928,645. Cobalt compounds yielding cobalt carbonyl hydrogen are used as catalysts in this case, optionally in the presence of metallic cobalt or iron. The conversion is carried out at 140° C. and at a synthesis gas pressure of 180 atmospheres.

UK Pat. No. 801,734 describes the use of rhodium-containing catalysts, which are present dissolved in the reaction mixture under the process conditions, for the hydroformylation of dicyclopentadiene. An unsaturated tricyclodecene-monoaldehyde having a structure not described in more detail is obtained in a yield of 68 percent as reaction product under the reaction conditions employed, namely, a temperature of 100° C. and a pressure of approximately 197 atmospheres.

Of the two double bonds in the cyclopentadiene molecule, the double bond in the norbornene ring is generally the more reactive. It is therefore to be expected that hydroformylation will preferentially result in the formation of 8- and 9-formyltricyclo-[5,2,1,0$^{2,6}$]-decene-3.

It therefore became desirable to provide a process which yields the isomeric compounds 3- and 4-formyltricyclo-[5,2,1,0$^{2,6}$]-decene-8 in good yields by hydroformylation of the cyclopentene ring.

SUMMARY OF THE INVENTION

Surprisingly, it was found that the hydroformylation of dicyclopentadiene at temperatures of 110° to 150° C. and pressures of 50 to 400 atmospheres produces 3- and 4-formyltricyclo-[5,2,1,0$^{2,6}$]-decene-8 in a high yield if the conversion is carried out in the presence of 1 to 30 ppm of rhodium, based on the amount of dicyclopentadiene employed, said rhodium being present in the form of an organic phosphine-carbon monoxide containing complex.

By maintaining a very low concentration of rhodium, namely, 1 to 30 ppm of rhodium based upon the amount of dicyclopentadiene, the hydroformylation of dicyclopentadiene produces 3- and 4-formyltricyclo-[5,2,1,0$^{2,6}$]-decene-8 in high yields. The rhodium complex compound is preferably used in an concentration of 10 to 20 ppm of metallic rhodium. The rhodium can be added to the reaction mixture in the form of rhodium sesquioxide. It is, however, also possible to add rhodium in another form, e.g., as rhodium trichloride, as the nitrate, sulfate, 2-ethylhexanoate (salt of 2-ethylhexanoic acid), or also as the metal. Under the reaction conditions and in the presence of organic phosphines, a soluble, catalytically active rhodium complex compound is formed, which also contains carbon monoxide in addition to phosphine. Obviously, this compound can also be prepared separately before the actual hydroformylation and then subsequently added to the reaction mixture. Finally, one can add the rhodium in combination with a carrier, in which case it is expedient for the rhodium compound to be present in an amount of approximately 1 to 40 percent by weight referred to the carrier.

The use of organic phosphines, e.g., triaryl, especially triphenyl, and in particular trialkyl, especially $C_{1-8}$ alkyl, phosphines, in conjunction with the rhodium complex compounds as catalyst is particularly important. These phosphines can exist not only in the form of complexes but also as free compounds in the reaction mixture. Their concentration should be 50 to 1,000 ppm, based on the rhodium. Concentrations of 100 to 600 have proven particularly suitable. Suitable triaryl phosphines are in particular triphenyl phosphine and tritolyl phosphine, and suitable trialkyl phosphines are in particular trioctyl phosphine. It is not necessary to use pure triaryl or trialkyl phosphines. Instead, mixtures of various triaryl or trialkyl phosphines can also be used.

Temperatures of 110° to 150° C., and in particular 120° to 140° C., have proven particularly suitable as the reaction temperature. Higher temperatures reduce the reaction time, but increase the formation of by-products such as aldols. The conversion is carried out at pressures of 50 to 400 atmospheres, advantageously in the range of from 200 to 300 atmospheres.

According to a preferred embodiment of the process in accordance with the invention, the conversion is carried out in the presence of an inert solvent. Suitable solvents are, for example, aliphatic and aromatic hydrocarbons such as heptane, hexane, cyclopentane and toluene. One to three parts by volume of solvent are preferably used per one part by volume of dicyclopentadiene.

Particularly contemplated types of phosphines include aliphatic straight or branched chained phosphines, cycloaliphatic phosphines, aromatic phosphines, arylaliphatic phosphines, phosphines with one or more substituted cyclic substituents and organic phosphines with two or more phosphorous atoms with from 1 to 30 carbon atoms. Examples of specific phosphines useful in the process of this invention are: tri-n-butylphosphine, tri-n-octylphosphine, tri-i-propylphosphine, dicyclohexylphosphine, tricyclohexylphosphine, diphenylphosphine, triphenylphosphine and 1,3-bis-(diphenylphosphino)-propane.

After the end of the hydroformylation, the reaction mixture is worked up by cooling and lowering the pressure of the reactor contents. After decomposing the rhodium carbonyl compounds, e.g., by introducing nitrogen, the isomeric monoaldehydes are distilled off. Small amounts of catalyst remaining in the crude product are thereby decomposed.

The process according to the invention can be carried out batchwise, as well as semi-continuously or fully continuously.

The aldehydes obtained according to the new method are used as components in perfume and fragrance compositions, as well as intermediates in the manufacture of synthetic rubber.

In order to more fully illustrate the nature of the invention and the manner of practicing the same, the following example is presented:

EXAMPLE

Preparation of 3-(4)-formyltricyclo-[5,2,1,0$^{2,6}$]-decene-8

200 g of dicyclopentadiene, 200 ml of toluene, 5 mg of rhodium (=25 ppm) in the form of rhodium-2-ethylhexanoate and 1,27 g of triphenylphosphine are placed in a 1 liter volume autoclave. After flushing with nitrogen, a mixture of carbon monoxide and hydrogen (volume ratio 1:1) is added to the reactor to a pressure of 100 atmospheres. The reactor contents are then heated to 130° C. and the pressure is raised to 270 atmospheres by pumping in CO/H$_2$ and is maintained constant during the reaction by the continuous addition of the gas mixture. After two hours, the reaction is discontinued and the reaction mixture is analyzed by gas chromatography. At a 98 percent conversion, the crude product contains 88 percent of 3-(4)-formyltricyclo-[5,2,1,0$^{2,6}$]-decene-8.

What is claimed is:

1. A process for preparing 3- or 4-formyltricyclo-[5,2,1,0$^{2,6}$]-decene-8 which comprises contacting dicyclopentadiene with carbon monoxide and hydrogen in the presence of a rhodium catalyst at 110° to 150° C. and 50 to 400 atmospheres, said catalyst being present in an amount of 1 to 30 ppm of rhodium, based upon the amount of dicyclopentadiene employed, said rhodium being present in the form of an organic phosphine - carbon monoxide containing complex, said organic phosphine being an aliphatic straight or branched chain phosphine, a cycloaliphatic phosphine, an aromatic phosphine or an arylaliphatic phosphine or a phosphine with one or more substituted cyclic substituents or an organic phosphine with two or more phosphorus atoms having from 1 to 30 carbon atoms.

2. A process according to claim 1 wherein said rhodium is present in an amount of 20-30 ppm, based on the amount of dicyclopentadiene employed.

3. A process according to claim 1 wherein said phosphine is a triaryl phosphine.

4. A process according to claim 1 wherein said phosphine is a trialkyl phosphine.

5. A process according to claim 1 wherein the phosphine is present in an amount of 50-1,000 ppm.

6. A process according to claim 1 wherein the phosphine is present in an amount of 100-600 ppm.

7. A process according to claim 1 wherein the process is carried out in an inert solvent.

8. A process according to claim 3 wherein said phosphine is triphenylphosphine or tritolylphosphine.

9. A process according to claim 4 wherein said trialkylphosphine is a C$_1$-C$_8$ trialkylphosphine.

10. A process according to claim 9 wherein said trialkylphosphine is trioctylphosphine.

11. A process according to claim 1 wherein said phosphine is tri-n-butylphosphine, tri-n-octylphosphine, tri-i-propylphosphine, dichlorohexylphosphine, trihexylphosphine, diphenylphosphine, triphenylphosphine or 1,3-bis-(diphenylphosphino)-propane.

12. A process according to claim 1 wherein the rhodium catalyst is one prepared by reaction of rhodium with said organic phosphine prior to the commencement of said process.

13. A process according to claim 12 wherein said rhodium catalyst is one obtained by the complexing of rhodium or compound thereof with said organic phosphine, said rhodium being in the form of rhodium sesquioxide, rhodium trichloride, a rhodium nitrate, a rhodium sulfate, rhodium-2-ethylhexanoate or rhodium metal.

14. A process according to claim 1 wherein said rhodium catalyst is formed in situ by contacting a rhodium compound or rhodium metal with said organic phosphine to obtain a rhodium-containing complex.

* * * * *

UNITED STATES PATENT AND TRADEMARK OFFICE
CERTIFICATE OF CORRECTION

PATENT NO. : 4,289,913
DATED : Sep. 15, 1981
INVENTOR(S) : Helmut Bahrmann et al It is certified that error appears in the above-identified patent and that said Letters Patent are hereby corrected as shown below:

Title Page Assignee    Delete "Bayer Aktiengesellschaft, Leverkusen" and insert --Ruhrchemie Aktiengesellschaft, Oberhausen--.

Signed and Sealed this

Eleventh Day of May 1982

[SEAL]

Attest:

GERALD J. MOSSINGHOFF

Attesting Officer    Commissioner of Patents and Trademarks